United States Patent
Von Hagen

(10) Patent No.: US 10,421,941 B2
(45) Date of Patent: Sep. 24, 2019

(54) PROCESS FOR IMPROVING THE SOLUBILITY OF CELL CULTURE MEDIA

(71) Applicant: Merck Patent GmbH, Darmstadt (DE)

(72) Inventor: Joerg Von Hagen, Pfungstadt (DE)

(73) Assignee: Merck Patent GmbH, Darmstadt (DE)

( * ) Notice: Subject to any disclaimer, the term of this patent is extended or adjusted under 35 U.S.C. 154(b) by 56 days.

(21) Appl. No.: 15/534,533

(22) PCT Filed: Nov. 13, 2015

(86) PCT No.: PCT/EP2015/002275
§ 371 (c)(1),
(2) Date: Jun. 9, 2017

(87) PCT Pub. No.: WO2016/091350
PCT Pub. Date: Jun. 16, 2016

(65) Prior Publication Data
US 2017/0321186 A1    Nov. 9, 2017

(30) Foreign Application Priority Data
Dec. 11, 2014   (EP) ..................................... 14004168

(51) Int. Cl.
*C12N 5/00*    (2006.01)

(52) U.S. Cl.
CPC ........ *C12N 5/0018* (2013.01); *C12N 2500/05* (2013.01); *C12N 2500/30* (2013.01); *C12N 2500/32* (2013.01); *C12N 2500/35* (2013.01); *C12N 2500/38* (2013.01); *C12N 2500/50* (2013.01); *C12N 2500/99* (2013.01)

(58) Field of Classification Search
None
See application file for complete search history.

(56) References Cited

U.S. PATENT DOCUMENTS

| | | | |
|---|---|---|---|
| 2001/0009679 A1* | 7/2001 | Chen | A23L 2/02 424/484 |
| 2008/0019883 A1* | 1/2008 | Fike | C12N 1/00 422/139 |
| 2015/0166949 A1 | 6/2015 | Von Hagen | |

FOREIGN PATENT DOCUMENTS

EP    2674482 A1    12/2013

OTHER PUBLICATIONS

Zimmer "Effect of Raw Materials and Productin Prcesses on Dry Powder Media Quality", Cell Culture World Congress, 2012, retrieved from the Internet (https://www.slideshare.net/pscad123/effect-of-raw-materials-and-production-processes-on-dry-powder-media-quality) (Year: 2012).*
Hanko et al. "Determination of amino acids in cell culture and fermentation broth media using anion-exchange chromatography with integrated pulsed amperometric detection." Analytical Biochemistry 324.1 (2004): 29-38. (Year: 2004).*
Hong et al. "Monitoring Cell Culture Media with the Waters Amino Acid Analysis Solution", Waters Corporation company webpage, copyright 2007; http://www.waters.com/webassets/cms/library (Year: 2007).*
International Search Report dated Jan. 21, 2016 issued in corresponding PCT/EP2015/002275 application (4 pages).
Written Opinion of the International Searching Authority dated Jan. 21, 2016 issued in corresponding PCT/EP2015/002275 application (6 pages).
A. Zimmer, "Effect of Raw Materials and Production Processes on Dry Powder Media Quality", Cell Culture World Congress (Feb. 29, 2012) XP055240359—Retrieved from the Internet.
"Cell Culture Media—Addressing Variability in Dry Powder Mammalian Cell Culture Media", Articles, Drug Development & Delivery (Jun. 1, 2013) XP055194700—Retrieved from the Internet.
J. Von Hagen, "Development of Novel Chemically Defined Media for CHO Cell Applications", (Jan. 1, 2013) XP055240357—Retrieved from the Internet.

* cited by examiner

*Primary Examiner* — Emily A Cordas
(74) *Attorney, Agent, or Firm* — Millen White Zelano & Branigan, PC

(57) ABSTRACT

The invention relates to a process for improving the solubility of dry cell culture media. Some dry powder cell culture media show poor dissolving properties and result in turbid solutions when they are dissolved in aqueous solutions. Using a stepwise procedure in which the amino acids present in the non-dissolving part are identified and added to a new batch in other particle sizes significantly reduces that problem.

14 Claims, 2 Drawing Sheets

PROCESS FOR IMPROVING THE SOLUBILITY OF CELL CULTURE MEDIA

The present invention relates to a process for improving the solubility of dry cell culture media. Some dry powder cell culture media show poor dissolving properties and result in turbid solutions when they are dissolved in aqueous solutions. Using a stepwise procedure in which the amino acids present in the non-dissolving part are identified and added to a new batch in other particle sizes significantly reduces that problem.

Cell culture media in aqueous solution can provide an environment which supports and maintains the growth of cells and/or maintains a desired physiological cellular condition adventitious to the targeted production of certain products.

Cell culture media comprise of a complex mixture of components, sometimes more than one hundred different components, depending on the type of organism whose growth and/or targeted physiological status shall be supported.

The cell culture media required for the propagation of mammalian, insect or plant cells are typically much more complex than the media to support the growth of bacteria, yeast or fungi.

The first cell culture media that were developed were complex media consisting of diverse mixtures of components which were very poorly chemically defined, poorly characterized and difficult to manufacture with a consistent quality, such as plasma, serum, embryo extracts, and/or other biological extracts or peptones. A major advance was thus made with the development of chemically defined media. Chemically defined media often comprise of but are not exclusively limited to amino acids, vitamins, metal salts, antioxidants, chelators, growth factors, buffers, hormones, and many more substances known to those expert in the art.

Some cell culture media are offered as sterile aqueous liquids. The disadvantage of liquid cell culture media is their reduced shelf life and difficulties for shipping and storage. As a consequence, many cell culture media are presently offered as finely milled dry powder mixtures. These are manufactured for the purpose of dissolving in water and/or aqueous solutions and in the dissolved state are designed, often with other supplements, for supplying cells with a substantial nutrient base for growth and/or production of biopharmaceuticals from said cells and/or used as a feed to supply cells when specific nutrients become limiting.

A limiting factor for the preparation and the use of cell culture media from dry powder is the poor solubility of some components resulting in turbid media. Turbid media cannot be reliably applied in cell culture as the liquid part of the turbid medium does not have a defined composition. Turbid media often lead to varying efficiency in e.g. cell growth. An amendment of the media composition or substitution of certain components is often unwanted. A mere reduction of the overall particle size of the media components does not lead to an improvement.

Consequently it would be favourable to find a way to improve the overall solubility of a given media composition.

It has been found that the particle size of the amino acid components of a dry cell culture medium significantly influences its dissolving properties. Improved dissolving properties can be found for media in which certain amino acids are present in certain particle size ranges whereby an iterative process is most suitable to identify the most favourable combination of the particle size ranges of the different amino acids.

The present invention is therefore directed to a process for improving the solubility of a dry cell culture medium by a) dissolving a dry cell culture medium in a solvent whereby a precipitate remains b) identifying the amino acid ingredients in the precipitate c) preparing at least 3 different new batches of a dry cell culture medium with the composition of the one provided in step a) whereby in all new batches the particle size of all ingredients beside the ones identified in step b) remains unchanged and the amino acid ingredients identified in step b) are admixed to the new batches as follows:
   - each amino acid ingredient admixed to a batch has a certain particle size range
   - different amino acid ingredients in one batch may have the same or different particle size ranges
   - either the particle size ranges of one amino acid ingredient or the combination of particle size ranges of two or more amino acid ingredients are different for each new batch d) separately dissolving each batch under the same conditions as in step a). This means that the same solvent and temperature is used as in step a) and that the amount of solvent is such that the same concentration as in step a) is obtained e) identifying the batch with the lowest amount of non-dissolved ingredients f) optionally repeating steps b) to e) one or several times whereby in step b) the batch with the lowest amount of non-dissolved ingredients (i.e. the one identified in step e) is used.

In a final step g) the cell culture medium with improved solubility can be prepared by preparing a dry cell culture medium with the composition of the one provided in step a) and wherein the ingredients have the particle size ranges of the batch with the lowest amount of non-dissolved ingredients identified in step e).

In a preferred embodiment, one particle size range is above 150 μm.

In another preferred embodiment, one particle size range is between 50 and 150 μm.

In another preferred embodiment one particle size range is below 50 μm.

In another embodiment, if only one amino acid ingredient is identified in step b), the particle size range for said amino acid ingredient is different for each new batch prepared in step c).

In another embodiment, if two or more amino acid ingredients are identified in step b), the combination of particle size ranges of the said amino acid ingredients differs in each new batch prepared in step c).

In one embodiment the cell culture medium of step a) is a mammalian cell culture medium.

In another embodiment, the cell culture medium of step a) is a chemically defined cell culture medium.

In a preferred embodiment if the following amino acids are present in the precipitate, at least one of the batches prepared in step c) comprises them in the following particle size ranges or in particle size ranges included in the following particle size ranges (e.g. 70 μm to 125 μm is included in 50 μm to 150 μm):

cysteine and tyrosine: particle size range below 50 μm proline, phenylalanine, tryptophan, serine and threonine: particle size range between 50 μm and 150 μm serine, isoleucine, leucine, glycine and phenylalanine: particle size range above 100 μm histidine: particle size range between 25 and 100 μm arginine, glutamic acid, aspartic acid and threonine: particle size range between 50 and 150 μm.

In a preferred embodiment, in step a) and d) between 50 and 1000 g of the dry cell culture medium are dissolved. That means between 50 and 1000 g of the dry cell culture medium are dissolved for the production of a batch. Preferably the same amount of dry cell culture medium is used for each batch when performing the method of the invention.

In a preferred embodiment, in step e) the batch with the lowest amount of non-dissolved ingredients is identified by measuring and comparing the NTU of the batches prepared in step d).

In another preferred embodiment, the amino acid ingredients in the precipitate are identified for example by chromatographic methods like reversed phase UPLC or AAA (amino acid analysis) for which the amino acids are labeled with a fluorophor, separated on a reversed phase chromatography column and detected via their absorption signal.

Figure 1:
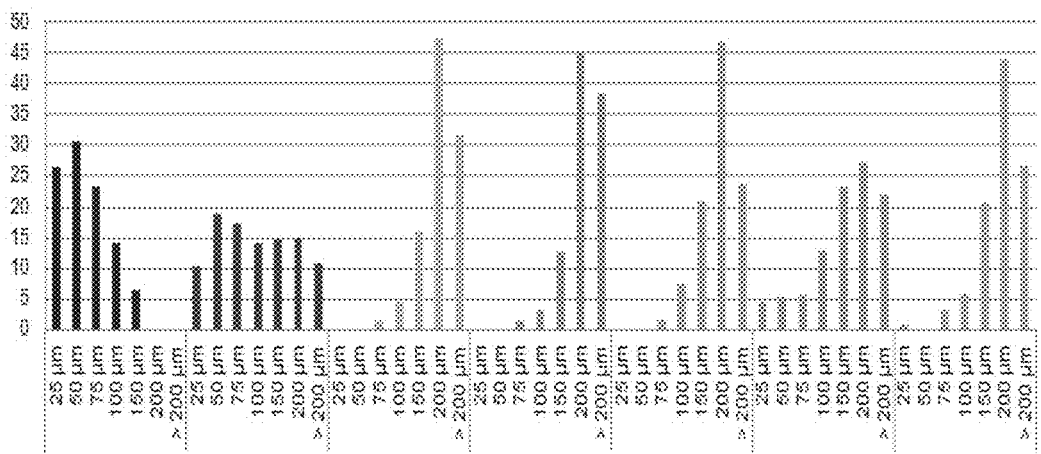
FIGS. 1 and 2 show particle size distributions of amino acids and the solubility of amino acids with such particle size distribution. Further information can be found in Example 2.

A cell culture medium to be improved by the method according to the present invention is any mixture of components which maintains and/or supports the in vitro growth of cells and/or supports a particular physiological state. It might be a complex medium or a chemically defined medium. The cell culture medium can comprise all components necessary to maintain and/or support the in vitro growth of cells or only some components so that further components are added separately. Examples of cell culture media according to the present invention are full media which comprise all components necessary to maintain and/or support the in vitro growth of cells as well as media supplements or feeds. In a preferred embodiment the cell culture medium is a full medium or a medium which lacks few components or a feed medium. Typically the cell culture medium to be improved according to the present invention has been prepared by mixing and milling all components of the medium together.

Typically, the cell culture media according to the invention are used to maintain and/or support the growth of cells and/or to support a particular physiological state in a bioreactor.

A mammalian cell culture medium is a mixture of components which maintain and/or support the in vitro growth of mammalian cells. Examples of mammalian cells are human or animal cells, preferably CHO cells, COS cells, I VERO cells, BHK cells, AK-1 cells, SP2/0 cells, L5.1 cells, hybridoma cells or human cells.

Chemically defined cell culture media are cell culture media that do not comprise any chemically undefined substances. This means that the chemical composition of all the chemicals used in the media is known. The chemically defined media do not comprise any yeast, animal or plant tissues; they do not comprise feeder cells, serum, extracts or digests or other components which may contribute chemically poorly defined proteins and/or peptides and/or hydrolysates to the media. Chemically undefined or poorly defined chemical components are those whose chemical composition and structure is not well known, are present in poorly defined and varying composition or could only be defined with enormous experimental effort—comparable to the evaluation of the chemical composition and structure of a protein like albumin or casein.

A powdered cell culture medium or a dry powder medium is a cell culture medium typically resulting from a milling process or a lyophilisation process. That means the powdered cell culture medium is a granular, particulate medium—not a liquid medium. The term "dry powder" may be used interchangeably with the term "powder;" however, "dry powder" as used herein simply refers to the gross appearance of the granulated material and is not intended to mean that the material is completely free of complexed or agglomerated solvent unless otherwise indicated.

Cells to be cultured with the media according to the present invention may be prokaryotic cells like bacterial cells or eukaryotic cells like yeast, fungi, plant or animal cells. The cells can be normal cells, immortalized cells, diseased cells, transformed cells, mutant cells, somatic cells, germ cells, stem cells, precursor cells or embryonic cells, any of which may be established or transformed cell lines or obtained from natural sources.

The size of a particle means the diameter of the particle. The particle diameter is determined by laser light scattering in silicone oil. Using this technique, the particle size is reported as a volume equivalent sphere diameter.

A particle size range gives the range of the particle size which 75% or more, preferably 85% or more of the particles have. That means if the particle size range is between 50 and 150 μm and if it is said that an amino acid ingredient has this particle size range, at least 75% of this amino acid ingredient is present in the form of particles which have a particle size between 50 and 150 μm. A particle size range of 50 to 150 μm also includes other, more narrow particle size ranges within this range, like 80 to 140 μm or 50 to 90 μm. That means particles having a particle size range of 80 to 140 μm are also covered by a particle size range of 0 to 150 μm. Particle size ranges of different amino acid ingredients or in different batches can be e.g. overlapping or can be included in another range or can be non-overlapping.

An amino acid ingredient is one type of amino acid present in the cell culture medium, e.g. tyrosine.

An inert atmosphere is generated by filling the respective container or apparatus with an inert gas. Suitable inert gases are noble gases like argon or preferably nitrogen. These inert gases are minimally-reactive and prevent undesirable chemical reactions from taking place. In the process according to the present invention, generating an inert atmosphere means that the concentration of oxygen is reduced below 10% (v/v) absolute, e.g. by introducing liquid nitrogen or nitrogen gas.

Different types of mills are known to a person skilled in the art.

A pin mill, also called centrifugal impact mill, pulverizes solids whereby protruding pins on high-speed rotating disks provide the breaking energy. Pin mills are for example sold by Munson Machinery (USA), Premium Pulman (India) or Sturtevant (USA).

A jet mill uses compressed gas to accelerate the particles, causing them to impact against each other in the process chamber. Jet mills are e.g. sold by Sturtevant (USA) or PMT (Austria).

A FITZMILL® commercialized by Fitzpatrick (USA), uses a rotor with blades for milling.

A process that is run continuously is a process that is not run batchwise. If a milling process is run continuously it means that the media ingredients are permanently and steadily fed into the mill over a certain time.

The cell culture media to be improved according to the present invention typically comprise at least one or more saccharide components, one or more amino acids, one or more vitamins or vitamin precursors, one or more salts, one or more buffer components, one or more co-factors and one or more nucleic acid components.

The media may also comprise sodium pyruvate, insulin, vegetable proteins, digests or extracts, fatty acids and/or fatty acid derivatives and/or pluronic product components (block copolymers based on ethylene oxide and propylene oxide) in particular Poloxamer 188 sometimes called PLURONIC® F 68 or KOLLIPHOR® P 188 or LUTROL® F 68 and/or surface active components like chemically prepared non-ionic surfactants. One example of suitable non-ionic surfactant are difunctional block copolymer surfactants terminating in primary hydroxyl groups also called poloxamers, e.g. available under the trade name PLURONIC® from BASF, Germany.

Saccharide components are all mono- or di-saccharides, like glucose, galactose, ribose or fructose (examples of monosaccharides) or sucrose, lactose or maltose (examples of disaccharides).

Examples of amino acids according to the invention are the proteinogenic amino acids, especially the essential amino acids, Examples of amino acids are alanine, cysteine, cystine, aspartic acid, glutaminic acid, phenylalanine, glycine, histidine, isoleucine, lysine, leucine, methionine, asparagine, proline, hydroxyproline, glutamine, arginine, serine, threonine, valine, tryptophan and tyrosine. According to the invention, the name of the amino acid like "tyrosine" means the D- or L-form if applicable as well as the amino acid itself or any salt or derivative thereof, like the hydrochloride form or the sodium salt.

Examples of vitamins are Vitamin A (Retinol, retinal, various retinoids, and four carotenoids), Vitamin $B_1$ (Thiamine), Vitamin $B_2$ (Riboflavin), Vitamin $B_3$ (Niacin, niacinamide), Vitamin $B_5$ (Pantothenic acid), Vitamin $B_6$ (Pyridoxine, pyridoxamine, pyridoxal), Vitamin $B_7$ (Biotin), Vitamin $B_9$ (Folic acid, folinic acid), Vitamin $B_{12}$ (Cyanocobalamin, hydroxycobalamin, methylcobalamin), Vitamin C (Ascorbic acid), Vitamin D (Ergocalciferol, cholecalciferol), Vitamin E (Tocopherols, tocotrienols) and Vitamin K (phylloquinone, menaquinones). Vitamin precursors and analogues are also included.

Examples of salts are components comprising inorganic ions such as bicarbonate, calcium, chloride, magnesium, phosphate, potassium and sodium or trace elements such as Co, Cu, F, Fe, Mn, Mo, Ni, Se, Si, Ni, Bi, V and Zn. Examples are copper(II) sulphate pentahydrate ($CuSO_4.5H_2O$), sodium chloride (NaCl), calcium chloride ($CaCl_2.2H_2O$), potassium chloride (KCl), Iron(II)sulphate, sodium phosphate monobasic anhydrous ($NaH_2PO_4$), magnesium sulphate anhydrous ($MgSO_4$), sodium phosphate dibasic anhydrous ($Na_2HPO_4$), magnesium chloride hexahydrate ($MgCl_2.6H_2O$), zinc sulphate heptahydrate.

Examples of buffers are $CO_2/HCO_3$ (carbonate), phosphate, HEPES, PIPES, ACES, BES, TES, MOPS and TRIS.

Examples of cofactors are thiamine derivatives, biotin, vitamin C, NAD/NADP, cobalamin, vitamine B12, flavin mononucleotide and derivatives, glutathione, heme, nucleotide phophates and derivatives.

Nucleic acid components, according to the present invention, are the nucleobases, like cytosine, guanine, adenine, thymine or uracil, the nucleosides like cytidine, uridine, adenosine, guanosine and thymidine, and the nucleotides like adenosine monophosphate or adenosine diphosphate or adenosine triphosphate.

A medium might for example comprise one or more of the following compounds:
L-ASPARAGINE MONOHYDRATE
L-ISOLEUCINE
L-PHENYLALANINE
SODIUM L-GLUTAMATE MONOHYDRATE
L-LEUCINE
L-THREONINE
L-LYSINE MONOHYDROCHLORIDE
L-PROLINE
L-SERINE
L-ARGININE MONOHYDROCHLORIDE
L-HISTIDINE MONOHYDROCHLORIDE MONOHYDRATE
L-METHIONINE
L-VALINE
L-TYROSINE
L-CYSTEINE
L-CYSTINE
MONO-SODIUM-L-ASPARTATE-MONOHYDRATE
L-TRYPTOPHAN
CHOLINE CHLORIDE
MYO-INOSITOL
NICOTINAMIDE
CALCIUM-D(+) PANTOTHENATE
PYRIDOXINE HYDROCHLORIDE
THIAMINE CHLORIDE HYDROCHLORIDE
VITAMIN B12 (CYANOCOBALAMINE) MICRONIZED
BIOTIN
FOLIC ACID
RIBOFLAVIN
MAGNESIUM SULFATE ANHYDROUS
COPPER(II) SULFATE PENTAHYDRATE
ZINC SULFATE HEPTAHYDRATE
1,4-DIAMINOBUTANE DIHYDRCHLORIDE
AMMONIUM HEPTAMOLYBDATE TETRAHYDRATE
CADMIUM SULFATE HYDRATE
MANGANESE(II) CHLORIDE TETRAHYDRATE
NICKEL(II) CHLORIDE HEXAHYDRATE
SODIUM META SILICATE
SODIUM METAVANADATE
TIN(II) CHLORIDE DIHYDRATE
SODIUM SELENITE (ABOUT 45% SE)
SODIUM DIHYDROGEN PHOSPHATE MONOHYDRATE
AMMONIUM IRON(III) CITRATE (ABOUT 18% FE)

Freezing according to the present invention means cooling to a temperature below 0° C.

Turbid liquid cell culture media are liquid cell culture media comprising non-dissolved components.

NTU means Nephelometric Turbidity Unit. It is a unit used to describe the turbidity in aqueous samples. It is measured with a calibrated nephelometer. Water containing 1 milligram of finely divided silica per liter has a turbidity of 1 NTU. Calibration standards are commercially available. Liquid cell culture media with an NTU over 10 are typically also visually turbid and form a precipitate when being centrifuged.

A precipitate is any non-dissolved matter in a liquid. A precipitate can preferably be isolated from the liquid and its amino acid ingredients can be identified.

A cell culture medium forming a precipitate is a liquid cell culture medium that still comprises a precipitate. A cell culture medium forming a precipitate would typically show a visual precipitate at the bottom of the tube when being centrifuged (e.g. 50-100 ml of the cell culture medium at 5.000 to 10.000 g).

The gist of the present invention is to provide powdered cell culture media that can be easily processed without clumping. When the dry powder media are dissolved in a suitable solvent by admixing the powder and the solvent, the powder dissolves and produces a liquid cell culture medium such as a full medium, a medium supplement, a medium subgroup or a feed with a desired and homogenous concentration of the media components.

The simple dissolving of a powdered cell culture medium is often complicated by substances which have a poor solubility in aqueous solvents. L-tyrosine for example has a solubility of 0.4 g/l in water at a temperature of 25° C. Cysteine easily forms the dimer cystine which is also poorly soluble. Other amino acids like glycine, valine, leucine, isoleucine and proline have moderate solubility in water.

It has been found that instead of simply reducing the particle size of all media components, it is much more efficient to not only reduce but adjust the particle size of certain amino acids, whereby e.g. some amino acids are added in a particle size range below 50 μm, others in a particle size range between 50 and 150 μm and others in a particle size range above 150 μm. Also other particle size ranges might be applicable. It has been found that tyrosine and cysteine preferably have a particle size range below 50 μm and Pro, Phe, Trp, Ser, and Thr preferably have a particle size range between 50 and 150 μm. Other amino acids like His, Gln, Asp, Val, Ile and Glu preferably have a particle size range above 150 μm. But as cell culture media typically are complex mixtures of many compounds which depending on their purpose have a greatly differing composition, it has been found that for a given specific media composition the best way to improve its solubility is to use the process according to the present invention.

For this process, in a first step a dry cell culture medium is provided and dissolved in a suitable solvent. Typically the dry cell culture medium provided in step a) is a dry cell culture medium produced by the state of the art production technique in which all components are mixed and milled together.

The amount and type of the solvent depend on the composition and the aimed purpose of the cell culture medium. The amount of the solvent is e.g. typically lower for feed media compared to full media. A person skilled in the art is able to define the type and amount of solvent needed to generate the appropriate liquid medium.

Typical solvents are water (most particularly distilled and/or deionized water or purified water or water for injection) or an aqueous buffer.

The solvent may also comprise saline, soluble acid or base ions providing a suitable pH range (typically in the range between pH 1.0 and pH 10.0), stabilizers, surfactants, preservatives, and alcohols or other polar organic solvents.

The dissolving is preferably performed under reproducible conditions like temperature, pressure etc.

If the resulting liquid medium is turbid it is obvious that not all components are dissolved and thus the medium might not be reliably applicable in cell culture. In the art of cell culture media, liquid media with an NTU over 10 are typically regarded as too turbid and thus not reliably applicable. Consequently, according to the present invention a turbid cell culture medium typically has an NTU of 10 or more. But the decision whether a liquid medium is too turbid for being reliably applicable is dependent on many factor like e.g. the specific application of the medium and thus finally on the decision of the person skilled in the art. The process of the present invention can be applied for liquid media with a turbidity over and below 10 NTU as long as non-dissolved media components can be analyzed and identified.

In a second process step, the amino acid ingredients of the precipitate, i.e. of the non-dissolved media components, are identified.

In a preferred embodiment, the precipitate is isolated and then further analyzed for identification. Typically 50 to 100 ml of the liquid medium are sufficient to isolate the precipitate. Isolation can be done by any suitable method like filtration or centrifugation.

Analysis can be done by any method suitable to identify amino acids, like mass spectrometry or chromatographic methods, e.g. ICP MS, HPLC.

In the next step, three or more new batches of the dry cell culture medium are prepared, whereby the overall chemical composition of the medium is identical to the composition of the medium originally provided in the first step. Also the particle size range of all ingredients beside the amino acid ingredients identified as ingredients of the precipitate remains the same.

What is differing in the three or more batches is the particle size of the amino acid ingredients that have been identified as being part of the precipitate. That means the particle size of those amino acids that have not been fully dissolved is amended. The whole amount of such an amino acid ingredient that needs to be added to the media composition is added with a defined particle size range. All batches should contain the said amino acids in different particle size ranges or combinations of particle size ranges.

If only one amino acid has been identified as being present in the precipitate, this amino acid is added to the batches so that it has a different particle size range in each batch. Exemplary particle size ranges are below 50 μm
between 10 and 50 μm
between 20 and 75 μm
between 50 and 150 μm
above 100 μm
above 150 μm
above 180 μm In case of one amino acid, it could for example be added to the first batch with a particle range below 50 μm, to the second batch with a particle range between 50 and 150 μm and to the third batch with a particle range above 150 μm.

In case of two or more amino acids the combination of particle size ranges should be different in each batch, whereby of course single amino acid ingredients may have the same particle size range in two or more batches. In any case, each amino acid ingredient is added to a batch in one defined particle size range. An example is given in the following table:

|  | range in Batch 1 | range in Batch 2 | range in Batch 3 |
| --- | --- | --- | --- |
| Amino acid 1 | below 50 μm | above 180 μm | below 50 μm |
| Amino acid 2 | below 50 μm | above 180 μm | between 20 and 75 μm |
| Amino acid 3 | between 50 and 150 μm | above 180 μm | between 20 and 100 μm |

In case of three or more amino acids ingredients present in the precipitate, preferably 4 to 8 batches with different combinations of particle size ranges are prepared.

It would of course be favorable to have 100% of the above mentioned amino acids present in the indicated particle size ranges. But the production of the amino acids with such particle size ranges would be very complicated. It has been found that the positive effect of the present invention is also measurable if at least more than 60% (w/w), preferably more than 75% (w/w) of the amino acid is present in the indicated particle size range. Amino acids with such a particle size distribution can typically be prepared by standard milling processes.

The production of such batches is known to a person skilled in the art. The powdered cell culture media batches are preferably produced by mixing all components beside the amino acids which shall be added in the form of particles having a specific particle size range and milling them. The mixing of the components is known to a person skilled in the art of producing dry powdered cell culture media by milling. Preferably, the components are thoroughly mixed so that all parts of the mixture have nearly the same composition. The higher the uniformity of the composition, the better the quality of the resulting medium with respect to homogenous cell growth.

The milling can be performed with any type of mill suitable for producing powdered cell culture media. Typical examples are ball mills, pin mills, FRITZMILL® or jet mills. Preferred is a pin mill, a FRITZMILL® or a jet mill, very preferred is a pin mill.

A person skilled in the art knows how to run such mills.

A large scale equipment mill with a disc diameter of about 40 cm is e.g. typically run at 1-6500 revolutions per minute in case of a pin mill, preferred are 1-3000 revolutions per minute.

The milling can be done under standard milling conditions resulting in powders with particle sizes between 10 and 300 µm, most preferably between 25 and 100 µm.

Preferably, all components of the mixture which is subjected to milling are dry. This means, if they comprise water, they do only comprise water of crystallization but not more than 10%, preferably not more than 5% most preferred not more than 2% by weight of unbound or uncoordinated water molecules.

In a preferred embodiment, the milling is performed in an inert atmosphere. Preferred inert protective gas is nitrogen.

In another preferred embodiment, all components of the mixture are frozen prior to milling. Freezing of the ingredients prior to the milling can be done by any means that ensures a cooling of the ingredients to a temperature below 0° C. and most preferably below −20° C. In a preferred embodiment the freezing is done with liquid nitrogen. This means the ingredients are treated with liquid nitrogen, for example by pouring liquid nitrogen into the container in which the ingredients are stored prior to introduction into the mill. In a preferred embodiment, the container is a feeder. If the container is a feeder the liquid nitrogen is preferably introduced at the side or close to the side of the feeder at which the ingredients are introduced.

Typically the ingredients are treated with the liquid nitrogen over 2 to 20 seconds.

Preferably the cooling of the ingredients is done in a way that all ingredients that enter into the mill are at a temperature below 0° C., most preferred below −20° C.

In a preferred embodiment, all ingredients are put in a container from which the mixture is transferred in a feeder, most preferred in a metering screw feeder. In the feeder the ingredients are sometimes further mixed—depending on the type of feeder—and additionally cooled. The frozen mixture is then transferred from the feeder to the mill so that the mixture which is milled in the mill preferably still has a temperature below 0° C., more preferred below −20 ° C.

Typically the blending time, that means the residence time of the mixture of ingredients in the feeder is more than one minute, preferably between 15 and 60 minutes.

A metering screw feeder, also called dosage snail, is typically run at a speed of 10 to 200 revolutions per minute, preferably it is run at 40 to 60 revolutions per minute.

Typically, the temperature of the mill is kept between −50 and +30° C. In a preferred embodiment, the temperature is kept around 10° C.

The oxygen level during milling preferably is below 10% (v/v).

The process can be run e.g. batch-wise or continuously. In a preferred embodiment the process according to the present invention is done continuously by, over a certain time, permanently filling the mixture of ingredients into a feeder for cooling and permanently filling cooled mixture from the feeder into the mill.

The amino acids of certain particle size ranges can also be produced by milling. Details about how to run a milling process can be found above. The amino acids are preferably milled in pin mill or jet mill systems. The amino acids are then added to the other media components and the composition is thoroughly mixed. Preferably this is done by using the scale dependent blender systems.

The batches are then dissolved in the same solvent, under the same conditions (like temperature etc.) and with the same final concentration as in the first step (step a)) so that the solubility of the batches can directly be compared with each other and with the one of step a).

Afterwards, out of the prepared batches of liquid cell culture medium, the batch with the lowest amount of non-dissolved ingredients is chosen. This can be done e.g. by isolating and weighing the precipitate or preferably by measuring the turbidity, preferably by measuring the NTU. Consequently, preferably the batch with the lowest NTU is chosen.

If the turbidity of the chosen batch is low enough for the cell culture medium to be reliably applied in cell culture, the inventive process is over. For the given cell culture medium composition the chosen batch shows the particle size ranges for those amino acid ingredients that originally had been insufficiently soluble that are suitable to make those amino acid ingredients sufficiently soluble. That means for producing a dry cell culture medium with improved solubility, the amino acid ingredients identified in step b) should be added to said dry medium in the particle size ranges equivalent to those taken for the batch with the lowest NTU.

If the turbidity of the chosen batch is still too high, the process of the invention is repeated one or more times.

If—when repeating the procedure—the amino acid ingredients of the precipitate are identical to those identified before, batches with other combinations of particle size ranges should be prepared.

Often, when repeating the procedure the precipitate shows a reduced number of amino acid ingredients (e.g. 2 amino acid ingredients for the batch with the lowest NTU compared to 4 for the original medium of step a)) so that new batches with combinations of particle size ranges for those remaining amino acid ingredients are prepared.

In any case, for the preparation of the batches (either first time or following times) the particle size ranges can be chosen randomly and/or directed by the following preferred ranges:

cysteine and tyrosine: preferred particle size range below 50 µm, most preferred between 10 and 50 µm arginine, glutamic acid, aspartic acid and threonine: preferred particle size range between 50 and 150 µm, most preferred between 50 and 100 µm histidine: preferred particle size range between 25 and 100 µm serine, isoleucine, leucine, glycine and phenylalanine: preferred particle size range above 100 µm, most preferred above 150 µm The batch that is identified in step e) either the first time or after repeating steps b) to e) one or more times is the batch with the improved solubility. When preparing a cell culture medium of a given composition (the one provided in step a)) with improved solubility, the particle size ranges of all ingredients should be chosen identical to the ones of the batch identified in step e).

With the process according to the invention the solubility of cell culture media that have been prepared by a mixing and milling process in which all ingredients are milled together without adjusting the particle sizes of certain ingredients, especially amino acid ingredients, can be improved. By adjusting the particle size range of certain amino acids the overall solubility the medium is improved.

The cell culture media improved with the process of the present invention and comprising amino acids of certain particle sizes show better dissolving properties compared to standard media of the same composition which are produced by mixing all components and submitting them to milling. It is often possible to generate dry powder media according to the invention which can be easily dissolved in a suitable solvent whereby dry powder media of the same composition but not comprising the amino acids as particles of certain sizes show poor dissolution properties.

The process of the present invention is suitable for all types of cell culture media. It is especially suitable for concentrated cell culture media and feed media which are made lay dissolving more than 50 g, sometimes up to 150 g of the dry cell culture medium in 1 liter of solvent.

The entire disclosure of all applications, patents, and publications, especially corresponding EP 14004168.2 filed Dec. 11, 2014, cited above and below are hereby incorporated by reference.

EXAMPLES

TABLE 1

1. Exemplary process according to the invention

|   | | Molarity (mM) |
|---|---|---|
| 1 | HEPES_CCM | 96 |
| 2 | L-ARGININE MONOHYDROCHLORIDE | 43 |
| 3 | L-LYSINE MONOHYDROCHLORIDE | 47 |
| 4 | PYRUVIC ACID SODIUM SALt | 68 |
| 5 | L-LEUCINE | 55 |
| 6 | POLOXAMER 188 | 0.6 |
| 7 | POTASSIUM CHLORIDE | 63 |
| 8 | L-SERINE | 44 |
| 9 | L-VALINE | 39 |
| 10 | SODIUM CHLORIDE | 79 |
| 11 | L-THREONINE | 38 |
| 12 | L-PROLINE | 34 |
| 13 | L-PHENYLALANINE | 23 |
| 14 | L-ISOLEUCINE | 28 |
| 15 | L-HISTIDINE MONOHYDROCHLORIDE MONOHYDRATE | 15 |
| 16 | MAGNESIUM CHLORIDE HEXAHYDRATE | 29 |
| 17 | DI-SODIUM HYDROGEN PHOSPHAT ANHYDROUS | 18 |
| 18 | SODIUM DIHYDROGEN PHOSPHATE | 18 |

TABLE 1-continued

1. Exemplary process according to the invention

|   | | Molarity (mM) |
|---|---|---|
|  | MONOHYDRATE FOR THE PRODUCTION OF CCM | |
| 19 | MYO-INOSITOL | 13 |
| 20 | L-CYSTEINE HYDROCHLORIDE MONOHYDRATE | 13 |
| 21 | L-METHIONINE | 15 |
| 22 | CHOLINE CHLORIDE | 13 |
| 23 | L-TRYPTOPHAN | 8 |
| 24 | MAGNESIUM SULFATE ANHYDROUS | 9 |
| 25 | L-GLUTAMIC ACID | 4 |
| 26 | GLYCINE | 7 |
| 27 | HYPOXANTHINE MONOSODIUM | 2 |
| 28 | L-ALANINE | 4 |
| 29 | L-ASPARTIC ACID | 2 |
| 30 | CALCIUM CHLORIDE ANHYDROUS | 3 |
| 31 | FOLIC ACID | 0.5 |
| 32 | CALCIUM-D(+) PANTOTHENATE PH EUR, BP, USP, JP, FCC | 0.5 |
| 33 | VITAMIN B12 (CYANOCOBALAMINE) MICRONIZED | 0.09 |
| 34 | THIAMINE CHLORIDE HYDROCHLORIDE | 0.34 |
| 35 | 2'-DEOXYTHYMIDINE | 0.38 |
| 36 | NICOTINAMIDE | 0.63 |
| 37 | PYRIDOXAL HYDROCHLORIDE | 0.35 |

A dry powder cell culture medium with a composition according to Table 1 is produced by mixing all components and milling them in a pin mill (UPZ100, at 19200 rpm)

When preparing a liquid medium a precipitate remains. NTU of the medium is 11. The precipitate contains L-Lysine HCl, L-Leucine, L-Valin and L-Tryptophan.

The medium without these amino acids is prepared as above in a pin mill (UPZ100, at 19200 rpm). The four amino acids are added to different batches in differing particle size ranges. When dissolving the different batches under the same conditions one batch shows an NTU of 3.

2. Particle Size Ranges of Amino Acids.

Figure 2:
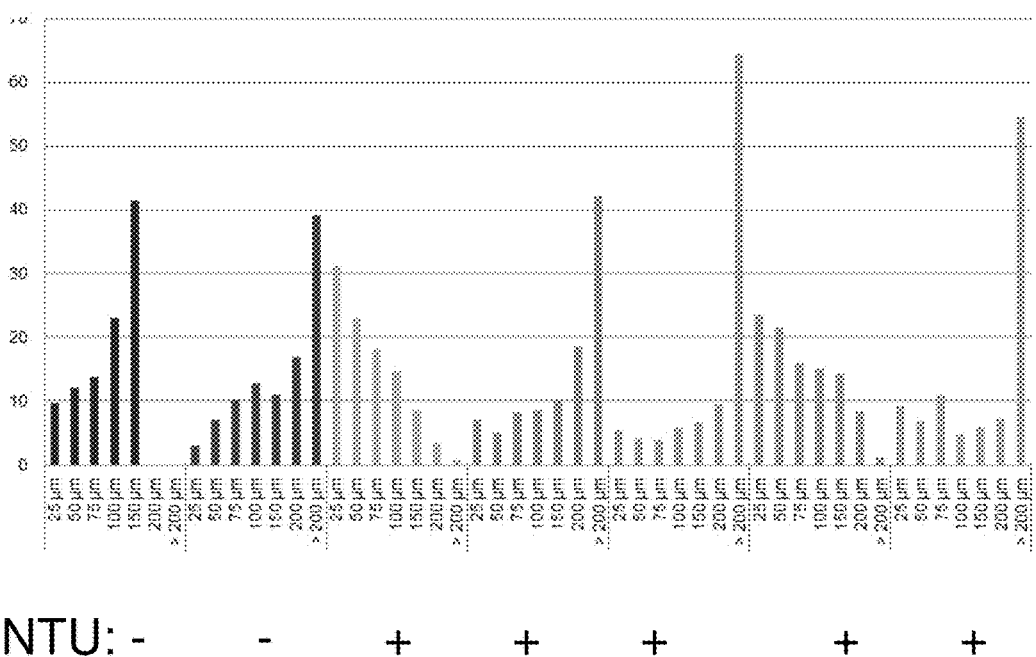

FIGS. 1 and 2 show 7 different particle size distributions of an amino acid (one amino acid in FIG. 1, another amino acid in FIG. 2). The x-axis shows the particle sizes, the y-axis the percentage frequency of the particle sizes. NTU +/− below the x-axis indicates for each batch if the particle size distribution results in a complete dissolution (+) or incomplete dissolution (−) in an otherwise soluble medium. This shows that the particle size distribution can influence the solubility of an amino acid—even if all other physical and chemical parameters are kept constant.

The invention claimed is:

1. A process for improving the solubility of a dry cell culture medium by
 a) dissolving a defined amount of dry cell culture medium in a defined amount of solvent whereby a precipitate remains,
 b) identifying the amino acid ingredients in the precipitate,
 c) preparing at least 3 different new batches of a dry cell culture medium with the composition of the one provided in step a) whereby in all new batches the particle size of all ingredients beside the ones identified in step b) remains unchanged and the amino acid ingredients identified in step b) are admixed to the new batches as follows:
  (i) each amino acid ingredient admixed to a batch has a certain particle size range,
  (ii) different amino acid ingredients in one batch have the same or different particle size ranges, and (iii) either the particle size ranges of one amino acid ingredient or the combination of particle size ranges of two or more amino acid ingredients are different for each new batch, d) separately dissolving each batch under the same conditions as in step a), e) identifying the batch with the lowest amount of non-dissolved ingredients, and f) optionally repeating steps b) to e) one or several times whereby in step b) the batch with the lowest amount of non-dissolved ingredients that has been identified in step e is used.

2. The process according to claim 1, wherein in step c) one particle size range is above 150 µm.

3. The process according to claim 1, wherein in step c) one particle size range is between 50 and 150 µm.

4. The process according to claim 1, wherein in step c) one particle size range is below 50 µm.

5. The process according to claim 1, wherein if only one amino acid ingredient is identified in step b), the particle size range for said amino acid ingredient is different for each batch when admixed to the batches in step c).

6. The process according to claim 1, wherein if two or more amino acid ingredients are identified in step b), the combination of particle size ranges differs from batch to batch.

7. The process according to claim 1, wherein the cell culture medium of step a) is a mammalian cell culture medium.

8. The process according to claim 1, wherein the cell culture medium of step a) is a chemically defined cell culture medium.

9. The process according to claim 1, wherein if the following amino acids are present in the precipitate, at least one of the batches prepared in step c) comprises them in the following particle size ranges or in particle size ranges included in the following particle size ranges:

(i) cysteine and tyrosine have a particle size range below 50 µm;

(ii) proline, phenylalanine, tryptophan, serine and threonine have a particle size range between 50 µm and 150 µm;

(iii) serine, isoleucine, leucine, glycine and phenylalanine have a particle size range above 100 µm;

(iv) histidine has particle size range between 25 and 100 µm; and (v) arginine, glutamic acid, aspartic acid and threonine have a particle size range between 50 and 150 µm.

10. The process according to claim 1, wherein in step a) and d) between 50 and 1000 g of the dry cell culture medium are dissolved.

11. The process according to claim 1, wherein in step e) the batch with the lowest amount of non-dissolved ingredients is identified by measuring and comparing the Nephelometric Turbidity Unit of the batches prepared in step d).

12. The process according to claim 1, wherein in step b) the amino acid ingredients in the precipitate are identified by amino acid analysis.

13. The process according to claim 1, wherein in step b) the amino acid ingredients in the precipitate are identified by reversed phase Ultra Performance Liquid Chromatography.

14. The process according to claim 1, wherein if the following amino acids are present in the precipitate, at least one of the batches prepared in step c) comprises them in the following particle size ranges or in particle size ranges included in the following particle size ranges:

(i) cysteine and tyrosine have a particle size range between 10 and 50 µm;

(ii) proline, phenylalanine, tryptophan, serine and threonine have a particle size range between 50 µm and 150 µm;

(iii) serine, isoleucine, leucine, glycine and phenylalanine have a particle size range above 150 µm;

(iv) histidine has particle size range between 25 and 100 µm; and (v) arginine, glutamic acid, aspartic acid and threonine have a particle size range between 50 and 100 µm.

* * * * *